United States Patent [19]

Miyazaki et al.

[11] Patent Number: 5,438,060
[45] Date of Patent: Aug. 1, 1995

[54] METHOD OF REDUCING ELEVATED INTRAOCULAR PRESSURE

[75] Inventors: Hirohisa Miyazaki, Osaka; Kumiko Fujinaga, Higashiosaka; Hitoshi Tanaka, Nara, all of Japan

[73] Assignee: Rohto Pharmaceutical Co., Ltd., Japan

[21] Appl. No.: 273,806

[22] Filed: Jul. 12, 1994

[30] Foreign Application Priority Data

Mar. 17, 1994 [JP] Japan .................................. 6-047096

[51] Int. Cl.$^6$ .......................................... A61K 31/505
[52] U.S. Cl. ...................................... 514/258; 514/913
[58] Field of Search ................................ 514/258, 913

[56] References Cited

PUBLICATIONS

The Merck Index, Eleventh Edition (1989), p. 529.

*Primary Examiner*—Zohreh Fay
*Attorney, Agent, or Firm*—Venable, Baetjer, Howard & Civiletti

[57] ABSTRACT

A method of reducing elevated intraocular pressure which comprises administering the compound of the formula (1):

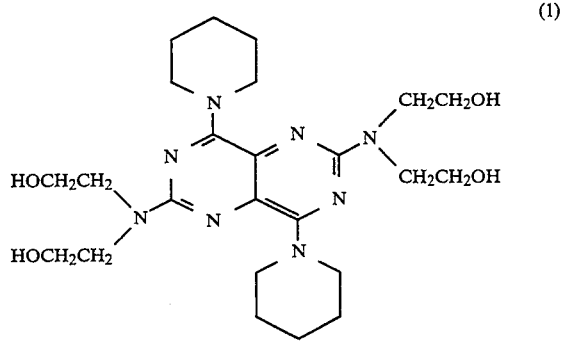

or a pharmaceutically acceptable salt thereof to patients suffering from abnormally elevated intraocular pressure is provided. A pharmaceutical formulation containing the compound of the formula (1) as an essential component is also provided.

2 Claims, 1 Drawing Sheet

METHOD OF REDUCING ELEVATED INTRAOCULAR PRESSURE

The present invention relates to a novel agent which is useful for the treatment of ocular hypertension (elevated intraocular pressure), and glaucoma. More specifically, this invention relates to a pharmaceutical composition for reducing elevated intraocular pressure which comprises as an essential component dipyridamole of the following formula (1) or any one of pharmaceutically acceptable salts thereof.

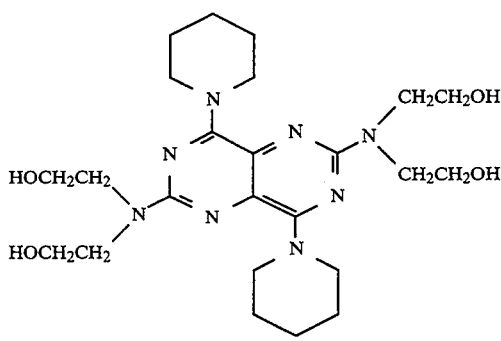

(1)

The present invention also relates to a method of reducing elevated intraocular pressure, which comprises administering the compound (1) to patients suffering from abnormally elevated intraocular pressure.

Glaucoma is a disease in which the intraocular pressure (IOP) is persistently or recurrently elevated above the normal range of pressure, which gives organic damage to ocular structures and further impairment of visual function which leads to, for instance, reduction of visual field. "Ocular hypertension" herein used is the term coined to denote an elevated intraocular pressure above the normal level, which is not accompanied by any functional impairment of vision, but, after a long period of time, may develop glaucoma. The medical treatment of ocular hypertension or glaucoma is directed to the reduction of the elevated intraocular pressure down to the normal IOP that induces no functional impairment, and also directed to the maintenance of the normal IOP.

In the present specification, an agent which is useful for reducing elevated intraocular pressure which is found in the ocular hypertension and glaucoma may sometimes be referred to as "antiglaucoma agent" for simplicity.

Conventional antiglaucoma agents known to be effective in the treatment of ocular hypertension or glaucoma are: carbonic anhydrase inhibitors (oral administration), hyperosmotic agents (injection), pilocarpine, epinephrine and its prodrug dipivefrine (eye drops). More recently, $\beta$-blockers (eye drops) are being extensively used for this purpose. However, all these agents have many disadvantages. Carbonic anhydrase inhibitors, for example, are known to have side effects such as gastrointestinal disturbances and general malaise. Hyperosmotic agents are used mainly in the treatment of acute attacks due to postoperative sudden rise in IOP and are not appropriate for the long-term therapy for glaucoma or ocular hypertension.

Pilocarpine eye drops are known to have several side effects such as feeling of obfuscation due to miosis-induced arctation of the visual field and accommodation disorders due to contraction of the ciliary muscle. Epinephrine and dipivefrine eye drops induce rebound congestion due to vasoconstriction, ophthalmalgia and tachycardia. The eye drops containing $\beta$-blockers as an active ingredient have been reported to cause systemic side effects such as headache and depression through their CNS (central nervous system) action, asthmatic symptoms by acting on the respiratory system and bradycardia and hypotension through its cardiovascular action (Iyaku Journal (Medicine and Drug Journal) 28: 705, 1992). When applied topically, $\beta$-blockers produce a feeling of dryness due to reduced lacrimal fluid and irritation at the time of instillation. These $\beta$-blockers are disadvantageous in that they are contraindicated for patients with bradycardia or bronchial asthma because the above side effects are particularly augmented in these patients (American Journal of Ophthalmology 102: 606, 1986). As described above, none of these antiglaucoma agents now in widespread use are satisfactory.

It is one objective of this invention to provide a novel antiglaucoma agent for treating ocular hypertension or glaucoma, which agent possesses an excellent ocular hypotensive effect (i.e., intraocular pressure-reducing effect) and no significant side effects, in particular, a minimal eye irritating effect.

As a result of extensive study seeking for excellent antiglaucoma agents, the present inventors have found that the compound (1) known as a therapeutic agent for treating angina pectoris has an ocular hypotensive effect, an effect unpredicted from the known major pharmacological effects, and minimal eye irritating effect, and therefore, the compound (1) is useful for the treatment of ocular hypertension or glaucoma.

The pharmacological properties of the compound (1) suggest that the compound (1) has no side effects such as miosis and accommodation disorders found in pilocarpine eye drops or rebound congestion due to vasoconstriction found in epinephrine and dipivefrine eye drops. The compound (1) is considered to have little effect on heart rate or blood pressue at the amount used in the eye drops of the present invention, and considered to have minor or no effect on respiratory system, since no side effects on respiratory system have been reported in connection with the compound (1). Accordingly, the compound (1) is considered to be free of hypotensive (blood pressure-reducing) effect, bradycardiac effect and side-effect on respiratory system, which are found in $\beta$-blocker used as eye drops.

As stated above, the compound (1) is a highly useful agent for the treatment of ocular hypertension or glaucoma without having significant side effects possessed by conventional agents.

Compound (1) is described in Japanese Pharmacopoeia, and it can be synthesized by referring, for example, to the published literatures listed under "3354. Dipyridamole" on page 529 in the 11th Edition of Merck Index. A commercially available compound (1) can also be used (Wako Junyaku Kougyou Co., Ltd.).

Examples of pharmaceutically acceptable salts of the compound (1), which can be the antiglaucoma agent of the present invention, are those formed with inorganic and organic acids, such as hydrochloride, sulfate, nitrate, phosphate, hydrobromate, tartrate, acetate, citrate, fumarate, maleate and oxalate.

The antiglaucoma agent of the present invention can be formulated in a pharmaceutical composition having an appropriate unit dosage form by mixing the compound of the formula (1) or a pharmaceutically acceptable salt thereof with conventional vehicles for pharmaceutical use. The unit dosage form can be any one of conventional dosage forms. Examples of the dosage forms for topical administration may be eye drops and eye ointments, and those for systemic administration may be tablets, granules and injections. It is particularly desirous to use the antiglaucoma agent of the present invention in the form of eye drops. Such eye drops may be aqueous formulations, gel formulations or oleaginous formulations.

When used as eye drops, it is desirable to prepare the formulation which contains the compound (1) at a concentration ranging preferably from 0.00005 to 0.5 w/v %, more preferably from 0.0001 to 0.1 w/v %. Additives that are usually used in formulating eye drops can be used together with the compound (1). Additives to be used include preservatives such as chlorobutanol, sodium dehydroacetate, benzalkonium chloride, cetylpyridinium chloride, phenethyl alcohol, methyl paraoxybenzoate and benzethonium chloride, buffering agents such as borax, boric acid and potassium dihydrogen phosphate, viscosity-increasing agents such as methylcellulose, hydroxyethylcellulose, carboxymethylcellulose, hydroxypropyl methylcellulose, polyvinyl alcohol, sodium carboxymethylcellulose and chondroitin sulfate, solubilizing agents such as polysorbate 80 and polyoxyethylene hydrogenated castor oil 60, and stabilizers such as disodium edetate and sodium bisulfite. It is desirable that eye drops are isotonic with lacrimal fluid, and, for this reason, isotonicating agents such as sodium chloride, potassium chloride, and glycerin may be added as necessary. The pH of the formulation may be at any point within an ophthalmologically acceptable range and is preferably between pH 5.0 and pH 8.0. In the case of eye drops having little buffer capacity, even those at a pH between pH 3.0 and pH 5.0 are acceptable because the pH will rapidly approximate to that of lacrimal fluid upon instillation. For preparing eye ointments, any conventional base such as ophthalmologic white petrolatum, propeto or plastibase may be used. Additives such as liquid paraffin may be used.

The dosage and administration mode of the eye drops of the present invention can vary depending on patients' conditions and age. The usual single dosage, however, is 1–3 drops and administered one to four times daily. For ophthalmic ointments, an appropriate amount is placed in the conjunctival sac one to two times daily.

Daily dose of dipyridamole may vary from 25 μg to 6 mg. LD50 values for dipyridamole in mice are 2150 mg/kg for oral administration, 2700 mg/kg for subcutaneous administration and 150 mg/kg for intravenous injection.

Figure 1:
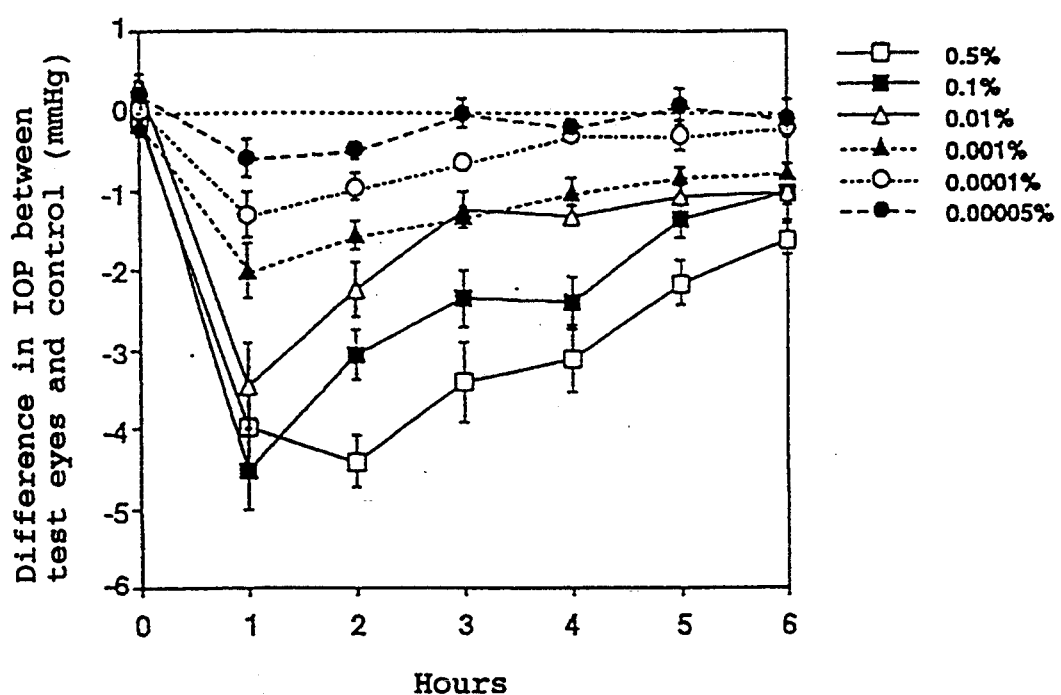
FIG. 1 shows the test results on the major pharmacology (ocular hypotensive effect) of the eye drops of the present invention.

The present invention is explained in more detail below by Examples and Experiments, but this invention is not limited to these Examples and Experiments.

| Example 1 Eye Drops | |
| --- | --- |
| Dipyridamole | 0.500 g |
| Glycerin | 2.122 g |
| Benzalkonium chloride | 0.010 g |
| 5N Hydrochloric acid | 0.200 ml |
| 10N Sodium hydroxide | appropriate amount |
| Sterile distilled water | appropriate amount |
| Total | 100 ml |

Production: Dipyridamole and 5N hydrochloric acid are dissolved in sterile distilled water (90 ml), and then glycerin, benzalkonium chloride, and 10N sodium hydroxide are added thereto and admixed. Sterile distilled water is added to the mixture to make the total volume 100 ml. pH: about 4; osmotic pressure-ratio: about 1.

| Example 2 Eye Drops | |
| --- | --- |
| Dipyridamole | 0.100 g |
| Glycerin | 2.297 g |
| Benzalkonium chloride | 0.010 g |
| 5N Hydrochloric acid | 0.100 ml |
| 10N Sodium hydroxide | appropriate amount |
| Sterile distilled water | appropriate amount |
| Total | 100 ml |

Production: Eye drops containing the above ingredients are prepared in the similar manner to that described in Example 1. pH: about 5; osmotic pressure-ratio: about 1.

| Example 3 Eye Drops | |
| --- | --- |
| Dipyridamole | 0.010 g |
| Boric acid | 1.237 g |
| Borax | 0.193 g |
| Sodium chloride | 0.134 g |
| Benzalkonium chloride | 0.010 g |
| 5N Hydrochloric acid | 0.100 ml |
| Sterile distilled water | appropriate amount |
| Total | 100 ml |

Production: Dipyridamole and 5N hydrochloric acid are dissolved in sterile distilled water (90 ml), and then boric acid, borax, sodium chloride, and benzalkonium chloride are added thereto and admixed. Sterile distilled water is added to the mixture to make the total volume 100 ml. pH: about 5; osmotic pressure-ratio: about 1.

| Example 4 Eye drops | |
| --- | --- |
| Dipyridamole | 0.010 g |
| Potassium dihydrogen phosphate | 0.799 g |
| Disodium hydrogen phosphate 12 $H_2O$ | 0.277 g |
| Sodium chloride | 0.506 g |
| Benzethonium chloride | 0.010 g |
| 5N Hydrochloric acid | 0.100 ml |
| Sterile distilled water | appropriate amount |
| Total | 100 ml |

Production: Dipyridamole and 5N hydrochloric acid are dissoleved in sterile distilled water (90 ml), and then potassium dihydrogen phosphate, disodium hydrogen phosphate 12 $H_2O$, sodium chloride and benzethonium chloride are added thereto and admixed. Sterile distilled water is added to the mixture to make the total volume 100 ml. pH: about 5; osmotic pressure-ratio: about 1

| Example 5 Eye drops | |
| --- | --- |
| Dipyridamole | 0.010 g |
| Liquid paraffin | appropriate amount |
| Total | 100 g |

Produnction: Eye drops containing the above ingredients are prepared sterilely in the following manner. Dipyridamole is ground in a mortar, small amount of liquid paraffin is then added thereto and admixed thoroughly. The mixutre is transferred to a dry container, the mortar is washed with small amount of liquid paraffin and remainder of liquid paraffin is then added to the container to make the total weight 100 g. The resultant mixture is stirred to obtain a homogeneous mixture.

| Example 6 Eye ointment | |
| --- | --- |
| Dipyridamole | 0.100 g |
| Liquid paraffin | 5.000 g |
| Ophthalmologic white petrolatum | appropriate amount |
| Total | 100 g |

Production: Eye ointment containing the above ingredients is prepared sterilely in the following manner. Dipyridamole is ground in a motar, liquid paraffin is then added thereto and admixed thoroughly. The mixture is then admixed with ophtalmologic white petrolatum.

Experiment 1: Main pharmacodynamics and pharmacology (ocular hypotensive effect)

The ocular hypotensive effect of the eye drops of this invention was investigated in rabbits. The same experiment was also conducted using a representative β-adrenergic blocking agent, and its ocular hypotensive effect was compared with that of eye drops of this invention.

Methods: According to the formulations described in Examples 1 and 2, six kinds of eye drops respectively containing 0.00005, 0.0001, 0.001, 0.01, 0.1 and 0.5% of the compound (1) were prepared. As a negative control, eye drops not containing compound (1), which were prepared according to the method described in Example 1, were used. The positive control was commercially available eye drops containing timolol maleate (0.5% equivalent of free base) as an active ingredient.

Male Japanese White rabbits (body weight: ca. 2 kg) with normal intraocular pressure were used in the experiment. Each of the test solutions (six kinds of eye drops containing 0.00005, 0.0001, 0.001, 0.001, 0.1 or 0.5% of dipyridamole) (50 μl) was instilled into one eye of each rabbit, and the control solution free of dipyridamole (50 μl) into the fellow eye which served as a control. For each solution, five rabbits were used. After anesthesia of the corneal surface by instillating 5 μl of 0.4%. oxybuprocaine hydrochloride, the intraocular pressure was measured using an applanation pneumatonograph (Alcon) before and after the instillation of the test solution and control solution. Measurement of intraocular pressure after the instillation was conducted with one-hour intervals until six hours post-instillation.

Results: The results of the above test involving the eye drops of the present invention are presented in FIG. 1, wherein difference in IOP between the control and the test eyes are shown. Table 1 compares the test results obtained with the commercial eye drops containing 0.5% timolol maleate as an active ingredient with those obtained with the eye drops of the present invention. The eye drops containing 0.1, 0.01, 0.001, 0.0001 or 0.00005% of compound (1) produced the maximal IOP reduction one hour after instillation. In the case of the 0.5% eye drops, the maximal IOP reduction was observed two hours after instillation. As for the 0.1% eye drops, an average difference of the IOP from the control eye drops was 4.5 mmHg, and this ocular hypotensive effect was retained for six hours after instillation. Such ocular hypotensive effect obtained by the instillation of 0.5, 0.01 or 0.001% eye drops remained unchanged six hours after instillation. In the cases of 0.001 and 0.0005% eye. drops, ocular hypotensive remained unchanged 2.0 hours after instillation.

On the other hand, commercially available timolol eye drops (0.5%) produced IOP reduction of 0.8 mmHg one and two hours after instillation. The degree of the IOP reduction by the timolol eye drop was significantly less than that by the 0.0001% eye drops of the present invention which produced IOP reduction of 1.3 mmHg and 1.0 mmHg one and two hours after instillation, respectively. Thus, the eye drops of the present invention produces the same or greater effect as the timolol eye drops at a 1/5000 concentration.

These results show the excellent ocular hypotensive effect of the eye drops of the invention which is superior to that of the typical commercial eye drops containing β-adrenergic blocker.

TABLE 1

| | Difference in IOP between the control and test eyes (mmHg) | | | | |
| --- | --- | --- | --- | --- | --- |
| drug | Concentration of free base (%) | 1 hr | 2 hr | 4 hr | 6 hr |
| Compound (1) | 0.5 | −3.94 | −4.40 | −3.10 | −1.60 |
| Compound (1) | 0.1 | −4.50 | −3.05 | −2.40 | −1.00 |
| Compound (1) | 0.01 | −3.44 | −2.25 | −1.31 | −1.00 |
| Compound (1) | 0.001 | −2.00 | −1.56 | −1.00 | −0.75 |
| Compound (1) | 0.0001 | −1.30 | −0.95 | −0.30 | −0.20 |
| Compound (1) | 0.00005 | −0.60 | −0.50 | −0.20 | −0.10 |
| Timolol maleate | 0.5 | −0.80 | −0.80 | −0.25 | −0.10 |

Experiment 2: Eye irritation test

The eye irritating effect of the eye drops of the present invention was investigated in rabbits.

Methods: According to the descriptions in Experiment 1, various kinds of eye drops containing different concentrations of compound (1) as an active ingredient were prepared, and their eye irritating effects were evaluated by modified Draize test (Gendaino Rinsho (Modern Clinics) 4: 277, 1970).

Male Japanese White rabbits (body weight: ca. 2 kg) were used in the experiment. The test solutions containing compound (1) at various concentration (50 μl) was instilled into one eye of an animal and the control solution free from compound (1) into the fellow eye in the same manner. The degree of ocular irritation was assesed by scoring the preocular conditions before and 0.5, 1, 2, 3 and 6 hours after instillation according to the modified Draize method.

Results: The test results for the 0.5% eye drops of the invention which has the highest concentration with respect to compound (1) are shown in Tables 2 and 3. In the iris, a slight congestion was observed 0.5 hours after instillation of the test solution. However, the congestion disappeared after 6 hours. This effect causes no clinical problem since increased amount of intraocular blood flow is disirable in the treatment of glaucoma. For the tunica conjunctiva bulbi, the score for the test solution was slightly higher than that for the control solution, but such difference was negligible. With respect to the other items, there was no difference between the test solution and the control solution irrespective of the time when the degree of irritation was measured. Thus, the experiment results demonstrate that the eye drops of the present invention give negligible irritation to rabbit eyes.

TABLE 2

Degree of irritation on eyes for the 0.5% eye drops (Test solution) (Average score of four rabbits tested)

| | Time after instillation (hours) | | | | | |
| --- | --- | --- | --- | --- | --- | --- |
| | before instillation | 0.5 | 1 | 2 | 3 | 6 |
| Cornea: | | | | | | |
| Opacity degree of density | 0 | 0 | 0 | 0 | 0 | 0 |
| Area of cornea involved | 0 | 0 | 0 | 0 | 0 | 0 |
| Iris: | | | | | | |
| values | 0 | 0.5 | 1.0 | 0.8 | 0.5 | 0 |
| Conjunctivae: | | | | | | |
| Redness of tunica conjunctivae palpebrarum | 0.8 | 1.5 | 1.8 | 1.8 | 1.3 | 0.8 |
| Chemosis | 0 | 0 | 0 | 0 | 0 | 0 |
| Redness of tunica conjunctivae bulbi | 0.1 | 0.9 | 1.1 | 0.9 | 0.5 | 0.1 |
| Condition of haw | 0.4 | 0.6 | 0.5 | 0.5 | 0.5 | 0.5 |
| Discharge | 0 | 0 | 0 | 0 | 0 | 0 |

TABLE 3

Degree of irritation on eyes for the 0.5% eye drops (Control solution) (Average score of four rabbits tested)

| | Time after instillation (hour) | | | | | |
| --- | --- | --- | --- | --- | --- | --- |
| | before instillation | 0.5 | 1 | 2 | 3 | 6 |
| Cornea: | | | | | | |
| Opacity degree of density | 0 | 0 | 0 | 0 | 0 | 0 |
| Area of cornea involved | 0 | 0 | 0 | 0 | 0 | 0 |
| Iris: | | | | | | |
| values | 0 | 0 | 0 | 0 | 0 | 0 |
| Conjunctivae: | | | | | | |
| Redness of tunica conjunctivae palpebrarum | 0.9 | 1.5 | 1.5 | 1.3 | 1.3 | 0.8 |
| Chemosis | 0 | 0 | 0 | 0 | 0 | 0 |
| Redness of tunica conjunctiva bulbi | 0.3 | 0.3 | 0.3 | 0.4 | 0.3 | 0 |
| Condition of haw | 0.3 | 0.5 | 0.5 | 0.5 | 0.5 | 0.5 |
| Discharge | 0 | 0.3 | 0.3 | 0.3 | 0 | 0 |

The pharmaceutical composition of the present invention shows an excellent ocular hypotensive effect and a minimal eye-irritating effect, and these advantages promise that the composition of the present invention is highly useful in the treatment of ocular hypertension and glaucoma.

What is claimed is:

1. A method of reducing intraocular pressure which comprises administering an effective amount of the compound of the formula (1):

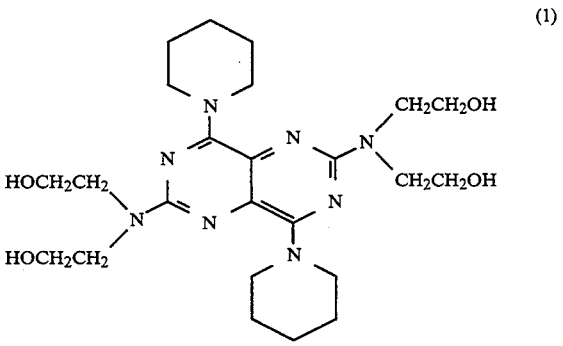

or a pharmaceutically acceptable salt thereof to patients sufferlag from elevated intraocular pressure.

2. The method as claimed in claim 1, wherein the comboand (1) is topically administered.

* * * * *